(12) United States Patent
Ohishi et al.

(10) Patent No.: US 9,011,944 B2
(45) Date of Patent: Apr. 21, 2015

(54) POLYPHENOL COMPOSITION

(75) Inventors: Susumu Ohishi, Tokyo (JP); Norihiko Satake, Tokyo (JP); Tomoko Konishi, Tokyo (JP); Shinichiro Takashima, Tokyo (JP)

(73) Assignee: Kao Corporation, Tokyo (JP)

( * ) Notice: Subject to any disclaimer, the term of this patent is extended or adjusted under 35 U.S.C. 154(b) by 96 days.

(21) Appl. No.: 13/260,140

(22) PCT Filed: Mar. 17, 2010

(86) PCT No.: PCT/JP2010/001907
§ 371 (c)(1),
(2), (4) Date: Sep. 23, 2011

(87) PCT Pub. No.: WO2010/109814
PCT Pub. Date: Sep. 30, 2010

(65) Prior Publication Data
US 2012/0015057 A1    Jan. 19, 2012

(30) Foreign Application Priority Data
Mar. 23, 2009    (JP) ................................ 2009-069691

(51) Int. Cl.
*A61K 36/00* (2006.01)
*A61K 36/82* (2006.01)
*A23L 1/30* (2006.01)
*A23F 3/16* (2006.01)

(52) U.S. Cl.
CPC .................. *A23L 1/3002* (2013.01); *A23F 3/16* (2013.01); *A23V 2002/00* (2013.01); *A61K 36/82* (2013.01)

(58) Field of Classification Search
None
See application file for complete search history.

(56) References Cited

U.S. PATENT DOCUMENTS

| | | | |
|---|---|---|---|
| 2006/0057261 A1* | 3/2006 | Ogura et al. | 426/330.3 |
| 2007/0178175 A1 | 8/2007 | Matsubara et al. | |
| 2009/0041921 A1 | 2/2009 | Maruyama et al. | |
| 2009/0053384 A1 | 2/2009 | Watanabe et al. | |
| 2010/0136205 A1 | 6/2010 | Konishi | |

FOREIGN PATENT DOCUMENTS

| | | |
|---|---|---|
| JP | 05 279264 | 10/1993 |
| JP | 6-9607 A | 1/1994 |
| JP | 2001 299264 | 10/2001 |
| JP | 2003 265135 | 9/2003 |
| JP | 2003 274890 | 9/2003 |
| JP | 2004 330005 | 11/2004 |
| JP | 2006-8580 A | 1/2006 |
| JP | 2006-129757 A | 5/2006 |
| JP | 2006-160656 | 6/2006 |
| JP | 2006 290756 | 10/2006 |
| JP | 2007-1893 | 1/2007 |
| JP | 2008-79609 | 4/2008 |
| JP | 2009-98 | 1/2009 |
| JP | 2009-29752 A | 2/2009 |
| WO | 2005 077384 | 8/2005 |
| WO | 2008/146479 | 12/2008 |

OTHER PUBLICATIONS

Zhu et al, Study on the determination of flavonols and its glycosides and their effects on the color of green tea infusion. Shipin Yu Fajiao Gongye (2009), 35(2), 146-150.*

Perva-Uzunalic et al, Extraction of active ingredients from green tea (*Camellia sinensis*): Extraction efficiency of major catechins and caffeine. Food chemistry, Jun. 2006 vol. 96, issue 4 p. 597-605.*

Yoshioka, H., et al., "Green Tea Extract/Chitosan Complex as a New Foodstuff," Chitin and Chitosan Research, vol. 12, No. 2, p. 214, (2006).

International Search Report Issued Jun. 8, 2010 in PCT/JP10/001907 Filed Mar. 17, 2010.

Japanese Notice of Information Offer Form issued on Dec. 20, 2011 with Information Offer Form filed by the applicant on Nov. 25, 2011, in Japan Patent Application No. 2010-060408 (with English Translation).

Office Action issued in Chinese Patent Application No. 201080013676.4 dated Oct. 19, 2012 with English translation (13 pages).

Ling Guanting, "Anti Oxidant Food and Health", Chemical Industry Press, First Edition, May 31, 2004, 2 pages with English translation.

Andreas Finger, et al., "Chromatography of tea constituents", Journal of Chromatography, vol. 624, No. 1-2, Oct. 30, 1992, pp. 293-315.

Daniele Del Rio, et al., "HPLC-MSn Analysis of Phenolic Compounds and Purine Alkaloids in Green and Black Tea", Journal of Agricultural and Food Chemistry, vol. 52, No. 10, May 19, 2004, pp. 2807-2815.

* cited by examiner

*Primary Examiner* — Qiuwen Mi
(74) *Attorney, Agent, or Firm* — Oblon, McClelland, Maier & Neustadt, L.L.P.

(57) ABSTRACT

A polyphenol composition derived from *Camellia sinensis* and contains flavonol aglycones and flavonol glycosides, in a weight ratio [(B)/(A)] of the following total contents (B) to (A) is from 0.01 to 18, wherein (A) total content of the flavonol aglycones contained in solids of the polyphenol composition after hydrolysis as measured by high-performance liquid chromatography, and (B) total content of the polyphenols contained in solids of the polyphenol composition as measured by the ferrous tartrate method.

20 Claims, 3 Drawing Sheets

POLYPHENOL COMPOSITION

FIELD OF THE INVENTION

This invention relates to a polyphenol composition obtained from *Camellia sinensis*.

BACKGROUND OF THE INVENTION

In recent years, reflecting diversification of consumers' tastes and increasing health consciousness, a wide variety of health foods have been put on the market and are finding a broadening demand. For example, polyphenols are known to have antioxidant activities, and owing to their expected effects such as anti-arteriosclerosis, antiallergy and blood stream enhancement, they are recognized as an important ingredient for health foods.

These polyphenols can be obtained, for example, as a polyphenol fraction by bringing an aqueous extract solution of oolong tea into contact with activated carbon or an adsorbent resin to eliminate the non-polymer catechins (Patent Document 1).

PRIOR ART DOCUMENT

Patent Document

Patent Document 1: WO2005077384

SUMMARY OF THE INVENTION

The present invention provides a polyphenol composition derived from *Camellia sinensis* and containing flavonol aglycones and flavonol glycosides, wherein:

a weight ratio [(B)/(A)] of the following total contents (B) to (A) is from 0.01 to 18:

(A) total content of the flavonol aglycones contained in solids of the polyphenol composition after hydrolysis as measured by high-performance liquid chromatography, and (B) total content of the polyphenols contained in solids of the polyphenol composition as measured by the ferrous tartrate method.

The present invention also provides a food and drink containing the polyphenol composition.

The present invention further provides a process for the production of the polyphenol composition, which includes:

a step for adsorbing a *Camellia sinensis* extract on a synthetic adsorbent, a step for bringing a first aqueous organic solvent solution into contact with the synthetic adsorbent to elute a first fraction, and a step for bringing a second aqueous organic solvent solution, which is higher in hydrophobicity than the first aqueous organic solvent solution, into contact with the synthetic adsorbent after the elution of the first fraction, thereby eluting a second fraction with the polyphenol composition contained therein.

DESCRIPTION OF THE INVENTION

Figure 1:
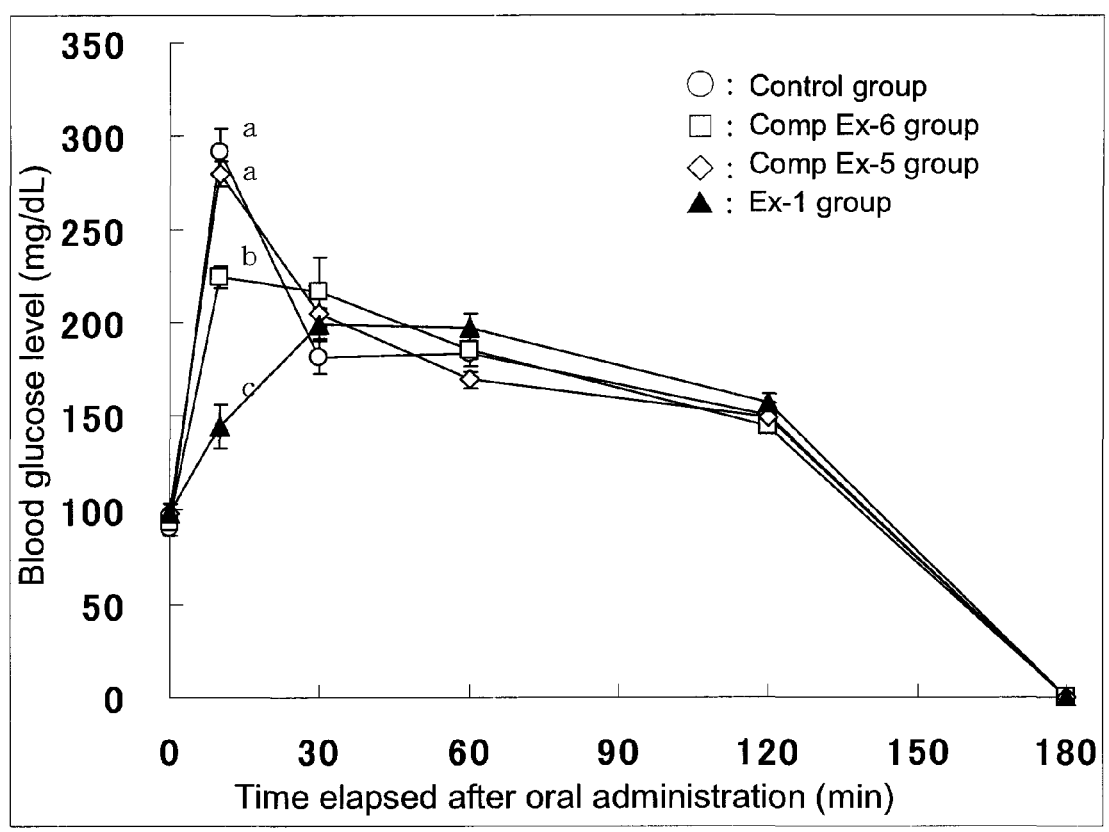
FIG. 1 is a diagram illustrating changes in postprandial blood glucose level in Test Example 1.

Polyphenols inherently have strong harshness so that, when contained in large quantities in a food and drink, their palatability is often impaired significantly.

The present inventors conducted various research on polyphenol compositions derived from *Camellia sinensis*. As a result, it has been found that the harshness inherent to polyphenols is markedly reduced when the content ratio of the flavonol aglycones to the flavonol glycosides in a polyphenol composition falls within a specific range.

According to the present invention, there is provided a polyphenol composition derived from *Camellia sinensis* and markedly reduced in the harshness inherent to polyphenols despite the inclusion of polyphenols at high concentration. This polyphenol composition has highly palatable bitterness not available from the non-polymer catechins or flavonols alone, but brings no discomfort in aftertaste even when the bitterness is lessened with a sweetener or seasoning. Accordingly, the polyphenol composition is suited for habitual intake as health foods or the like.

A description will first be made about terms to be used herein.

The term "polyphenols" as used herein means those which can be measured by the ferrous tartrate method. Specifically, flavonols, fravan-3-ols, proanthocyanidins, and their polymers can be exemplified. The flavonols include quercetin, myricetin, kaempferol, and their glycosides; the flavan-3-ols include catechins; and the polymers thereof include theaflavins, oolong homobisflavans or the like.

The term "*Camellia sinensis*" means a species of tea tree of the genus *camellia* (Theaceae), and depending upon the processing method, can be roughly divided into unfermented tea, semi-fermented tea and fermented tea. Among these, unfermented tea is preferred. Examples of the unfermented tea include green teas such as kukicha, boucha, mecha, sencha, bancha, tencha and kamairicha manufactured from tea selected from the Genus *Camellia*, for example, *C*. var. *sinensis* (including the *Yabukita* variety), *C*. var. *assamica*, or a hybrid thereof. Examples of semi-fermented tea include tekkannon, irotane, ougonkei, buigancha or the like, which are collectively called "oolong tea". Examples of fermented tea include Darjeeling, Uva, Keemun or the like, which are called "black tea". It is to be noted that the terms "unfermented tea, semi-fermented tea, fermented tea, green tea, oolong tea, and black tea" as used herein do not mean tea extracts provided for drinking but mean tea materials for obtaining the tea extracts.

The term "flavonol aglycones" as used herein is a generic term for a mixture composed of myricetin, quercetin and kaempferol. Further, the term "flavonol glycosides" as used herein means glycosides containing myricetin, quercetin or kaempferol as an aglycone skeleton, and includes those formed of these glycosides and sugars further attached thereto. The term "total content of the flavonol aglycones" as used herein is defined based on the total amounts of myricetin, quercetin and kaempferol contained in a solution obtained after hydrolysis of a polyphenol composition that contains these flavonol aglycones and flavonol glycosides.

A description will next be made about the polyphenol composition according to the present invention.

The polyphenol composition according to the present invention is characterized by having the following total contents (A) and (B) at a specific ratio.

The total content (A) as used herein means the total content of the flavonol aglycones contained in solids of the polyphenol composition after hydrolysis as measured by high-performance liquid chromatography (hereinafter referred to as "the total content of the flavonol aglycones (A)"). The total content of the flavonol aglycones (A) may be preferably from 0.7 to 50 wt %, and from the viewpoints of taste and flavor and water solubility, more preferably from 1.5 to 45 wt %, more preferably from 5 to 40 wt %, more preferably from 7 to 35 wt %, even more preferably from 9 to 25 wt %.

Also, the total content (B) means the total content of the polyphenols contained in solids of the polyphenol composition as measured by the ferrous tartrate method (hereinafter referred to as "the total content of the polyphenols (B)"). The total content of the polyphenols (B) may be preferably from 5 to 95 wt %, and from the viewpoints of taste and flavor and water solubility, more preferably from 10 to 90 wt %, more preferably from 15 to 80 wt %, more preferably from 20 to 70 wt %, even more preferably from 25 to 40 wt %. It is to be noted that the term "solids" as used herein means a residue remaining after eliminating volatile substance such as water by drying a polyphenol composition for 3 hours in an electric constant-temperature drier controlled at 105° C.

The weight ratio [(B)/(A)] of the total content (B) to the total content (A) is from 0.01 to 18, and from the viewpoint of a reduction in harshness, may be preferably from 0.01 to 16, more preferably from 0.1 to 11, more preferably from 0.3 to 9, more preferably from 0.5 to 7, even more preferably from 1 to 5.

It is to be noted that "the total content of the flavonol aglycones (A)" and "the total content of the polyphenols (B)" are those quantitated by the methods described in examples to be described subsequently herein.

The polyphenol composition according to the present invention may also contain rutin. From the viewpoint of a reduction in harshness, it is preferred for the polyphenol composition according to the present invention to have a higher rutin content compared with conventional extracts (for example, green tea extracts, black tea extracts and oolong tea extracts) obtained from *Camellia sinensis* by extraction. Described specifically, the content of rutin (C) in the solids of the polyphenol composition may be preferably from 0.4 to 30 wt %, and from the viewpoint of a further reduction in harshness, more preferably from 0.8 to 25 wt %, more preferably from 2 to 20 wt %, more preferably from 4 to 15 wt %, even more preferably from 6 to 15 wt %. It is to be noted that the term "rutin" as used herein means one of flavonoid glycoside, specifically one made up of quercetin and β-rutinose (6-O-α-L-rhamnosyl-D-β-glucose) attached to the oxygen atom at the 3-position of the quercetin.

The polyphenol composition in which the weight ratio [(B)/(A)] and rutin content (C) fall within the above-described ranges, respectively, may be obtained, for example, by fractionating a *Camellia sinensis* extract through the below-described steps (1) to (3):

(1) a step for adsorbing the *Camellia sinensis* extract on a synthetic adsorbent, (2) a step for bringing a first aqueous organic solvent solution into contact with the synthetic adsorbent to elute a first fraction, and (3) a step for bringing a second aqueous organic solvent solution, which is higher in hydrophobicity than the first aqueous organic solvent solution, into contact with the synthetic adsorbent after the elution of the first fraction, thereby eluting a second fraction with the polyphenol composition contained therein.

As the *Camellia sinensis* extract for use in the step (1), it includes an extract obtained by extraction from *Camellia sinensis* with hot water or a water-soluble organic solvent. The *Camellia sinensis* extract may be used as it is or after drying or concentrating it. As the form of the tea extract, a liquid, slurry, semi-solid or solid may be exemplified. As an extraction method, a known method such as stirring extraction, column extraction or drip extraction may be adopted.

As a *Camellia sinensis* extract, it may be possible to use, instead of the above-described *Camellia sinensis* extract, a solution or dilution of a concentrated *Camellia sinensis* extract in/with water or an organic solvent or a *Camellia sinensis* extract and its concentrate in combination. It is to be noted that the term "concentrated *Camellia sinensis* extract" is one obtained by removing a part of a solvent from a *Camellia sinensis* extract. It may be prepared, for example, by the method described in JP-A-59-219384, JP-A-04-020589, JP-A-05-260907, JP-A-05-306279 or the like. As the concentrated *Camellia sinensis* extract, a commercially-available product may also be used. Examples include concentrated green tea extracts such as "POLYPHENONE" (product of Mitsui Norin Co., Ltd.), "TEAFURAN" (product of ITO EN, LTD.), "SUNPHENON" (product of Taiyo Kagaku Co., Ltd.), or the like.

As the *Camellia sinensis* extract, a green tea extract may be suitably used. If necessary, the *Camellia sinensis* extract may be subjected to treatment with tannase (JP-A-2004-321105), and subsequent to the treatment with tannase, to further treatment with at least one adsorbent selected from activated carbon, acid clay or activated clay (for example, JP-A-2007-282568).

Preferred as the synthetic adsorbent may be one formed of a polymer that has an ion exchange capacity of lower than 1 meq/g and an insoluble, three-dimensionally-crosslinked structure. The synthetic adsorbent may have any particle shape such as a spherical shape or irregular shape, but a spherical shape is preferred to satisfy good separation conditions.

Such a synthetic adsorbent may be manufactured by a known method, but a commercially-available product may be used. Commercially-available synthetic adsorbents include, for example, styrenic adsorbents such as "AMBERLITE XAD4, XAD16HP, XAD1180, XAD2000" (supplier: Rohm & Haas USA), "DIAION HP20, HP21" (products of Mitsubishi Chemical Corporation), "SEPABEADS SP-850, SP-825, SP-700, SP-70" (products of Mitsubishi Chemical Corporation), and "VPOC1062" (product of Bayer AG); substituted styrenic adsorbents with an enhanced adsorption capacity by the introduction of bromine atom in an aromatic ring, such as "SEPABEADS SP205, SP206, SP207" (products of Mitsubishi Chemical Corporation); methacrylic adsorbents such as "DIAION HP1MG, HP2MG" (products of Mitsubishi Chemical Corporation); phenolic adsorbents such as "AMBERLITE XAD761" (product of Rohm & Haas, Inc.); acrylic adsorbents such as "AMBERLITE XAD7HP" (product of Rohm & Haas, Inc.); polyvinyl adsorbents such as "TOYOPEARL HW-40C" (product of TOSOH CORPORATION); and dextran-based adsorbents such as "SEPHADEX LH-20" (product of Pharmacia AB).

Among these, those having styrenic, methacrylic, acrylic or polyvinyl matrices are preferred as synthetic adsorbents, with those having styrenic matrices being more preferred from the viewpoint of separation capacity.

As the amount of the synthetic adsorbent to be used, it is preferred from the viewpoint of separation capacity to choose such an amount that the ratio of the total weight of the non-polymer catechins in the *Camellia sinensis* extract to the total volume of the synthetic adsorbent falls within a range of from 20 to 60 g/L, with a range of from 25 to 55 g/L being more preferred and a range of from 30 to 50 g/L being even more preferred.

In the step (1), it is possible to adopt either a batch method or a column method. According to the batch method, the synthetic adsorbent is recovered by filtration after adding the synthetic adsorbent to the *Camellia sinensis* extract and stirring the resultant mixture to induce adsorption. According to the column method, on the other hand, adsorption treatment is continuously conducted through a column with the synthetic adsorbent packed therein. From the standpoint of productivity, the continuous treatment method making use of a column is preferred.

Upon subjecting the *Camellia sinensis* extract to the step (1), the concentration of the non-polymer catechins in the *Camellia sinensis* extract may desirably be adjusted to preferably from 0.5 to 10 wt %, more preferably from 0.8 to 5 wt % from the viewpoint of adsorption efficiency. To adjust the concentration of the non-polymer catechins in the *Camellia sinensis* extract to within the above-described range, the *Camellia sinensis* extract may be subjected to concentration, dilution or the like as needed.

As the first and second aqueous organic solvent solutions, aqueous solutions of organic solvents such as alcohols, e.g., ethanol or methanol, ketones, e.g., acetone, and esters, e.g., ethyl acetate may be exemplified. No particular limitation is imposed on the second aqueous organic solvent solution insofar as it is higher in hydrophobicity than the first aqueous organic solvent solution. As the second aqueous organic solvent solution, it is possible to use, for example, an aqueous solution containing an organic solvent at a higher concentration than the first aqueous organic solvent solution or an aqueous solution containing an organic solvent having a greater carbon number than the first aqueous organic solvent solution. The concentrations of the organic solvents in the first and second aqueous organic solvent solutions can be set as desired. For example, the concentration of the organic solvent in the first aqueous organic solvent solution may be preferably from 10 to 45 wt %, more preferably from 20 to 40 wt %, while the concentration of the organic solvent in the second aqueous organic solvent solution may be preferably from 50 to 98 wt %, more preferably from 50 to 95 wt %.

As specific operation methods for the steps (1) and (2), the methods described, for example, in JP-A-2006-160656, JP-A-2008-079609 or the like may be adopted.

A condition for passing the aqueous organic solvent solutions through a column can be set as desired. The conditions for the second aqueous organic solvent solution may be the same as or different from those for the first aqueous organic solvent solution. As the illustrative conditions for the first and second aqueous organic solvent solutions, the flow rate (SV) may be preferably from 0.5 to 10 [h−1], more preferably from 0.5 to 5 [h−1], and the flow ratio (BV) may be preferably from 0.5 to 10 [v/v], more preferably from 1 to 4 [v/v] relative to the volume of the synthetic adsorbent.

After the step (3), a hydrophobic polyphenol composition can be obtained by concentrating the second fraction. The concentration can be conducted by distillation, reduced-pressure distillation, rectification, thin-film distillation, membrane concentration or the like. Further, impurities may be separated as needed by filtration and/or centrifugation before or after the concentration. As the form of the polyphenol compositions, it includes various forms, such as solid, semisolid, liquid, slurry, or the like.

In the present invention, at least one ingredient selected from a *Camellia sinensis* extract, its concentrate, their purified products and other polyphenol compositions may be added to the polyphenol fraction to adjust the weight ratio [(B)/(A)] and the content of rutin (C) as desired. The term "purified product of a *Camellia sinensis* extract" as used herein means one obtained by removing, with a solvent and column, precipitates or the like from the *Camellia sinensis* extract or its concentrate. As the forms of the *Camellia sinensis* extract, its concentrate and their purified products, various forms can be exemplified including solid, aqueous solution and slurry. The "*Camellia sinensis* extract, its concentrate and their purified products" to be added to the polyphenol fraction may be one obtained from any *Camellia sinensis* of the same or different species as or from the polyphenol fraction. As the "other polyphenol compositions", on the other hand, polyphenol fractions obtained under different fractionation conditions and polyphenol fractions obtained from polyphenol-containing plants of different species can be exemplified.

The polyphenol composition according to the present invention has been reduced in the harshness inherent to polyphenols despite the inclusion of polyphenols at high concentration. The polyphenol composition according to the present invention has highly palatable bitterness not available from the non-polymer catechins or flavonols alone, but brings no discomfort in aftertaste even when the bitterness is lessened with a sweetener or seasoning. Accordingly, the polyphenol composition according to the present invention can be used by adding it to a food and drink.

The content of the polyphenol composition in the food and drink according to the present invention can be selectively determined depending upon the kind and/or form of the food and drink. In general, it may be from 0.1 to 10 wt % in terms of solids.

As beverages according to the present invention, tea beverages and non-tea based beverages can be mentioned, for example. Examples of the tea beverages include green tea beverages, oolong tea beverages, and black tea beverages. On the other hand, examples of the non-tea based beverages include non-alcoholic drinks such as refreshing drinks (e.g., fruit juices, vegetable juices, sports drinks, isotonic drinks, carbonated drinks), coffee drinks, nutritious supplement drinks, and beauty supplement drinks; and alcoholic drinks such as beer, wine, sake, plum-flavored spirits, sparkling liquors, whisky, brandy, distilled spirits, rum, gin, and liqueurs.

The beverage according to the present invention can be provided as a packaged beverage by filling the polyphenol composition as it is or after diluting it. An organic acid and/or its salt may be added to improve the water solubility of the polyphenol composition.

The organic acid may be aromatic or aliphatic, or may be a lactone, insofar as it contains one or more carboxyl groups in a molecule. Of these, a hydroxycarboxylic acid or its lactone is preferred. Specific examples include ascorbic acid, erythorbic acid, citric acid, gluconic acid, succinic acid, tartaric acid, lactic acid, adipic acid, fumaric acid, malic acid, or the like. Among these, ascorbic acid, citric acid, gluconic acid, tartaric acid, lactic acid and malic acid are preferred. As the salt, alkali metal salts, alkaline earth metal salts and amino acid salts may be mentioned. Among these, alkali metal salts are preferred, with sodium salts and potassium salts being more preferred.

Preferably, the organic acid and/or its salt may be added such that the concentration of organic acid ions in the beverage according to the present invention may fall within a range of from 1 to 100 mmol/L. From the viewpoints of improvements in solubility and appearance, the concentration of organic acid ions may be preferably from 2 to 95 mmol/L, more preferably from 5 to 90 mmol/L, more preferably from 10 to 85 mmol/L, more preferably from 15 to 80 mmol/L, more preferably from 18 to 70 mmol/L, even more preferably from 20 to 60 mmol/L. It is to be noted that, when the organic acid is an n-valent polycarboxylic acid, for example, the term "the concentration of organic acid ions" means the total concentration of carboxyl anions (COO⁻) which are in a dissociated state from the $1^{st}$ stage to the $n^{th}$ stage.

The beverage according to the present invention may contain additives commonly employed upon preparation of the food and drink, for example, antioxidants, bitterness/astringency suppressors, vitamins, flavorings, various esters, inorganic acids, inorganic acid salts, inorganic salts, colorants, emulsifiers, preservatives, seasonings, sweeteners, sour seasonings, fruit extracts, vegetable extracts, flower honey extracts, pH adjustors and quality stabilizers, and further, plant extracts such as coffee extracts, either singly or in combination.

The pH (25° C.) of the beverage according to the present invention may be adjusted to preferably from 2 to 9, and from the viewpoints of taste and flavor and appearance, more preferably from 2.5 to 8, more preferably from 3 to 7.0, even more preferably from 3.5 to 6.5.

As a package filled with the beverage according to the present invention, a package of a conventional form, such as a molded package made of polyethylene terephthalate as a principal component (a so-called PET bottle), a metal can, a paper package combined with metal foils or plastic films, a bottle or the like, can be mentioned as for general beverages.

The packaged beverage can be produced, for example, by filling the beverage in a package like a metal can and, when heat sterilization is feasible, conducting heat sterilization under sterilization conditions prescribed in relevant regulations (in Japan, the Food Sanitation Act). For those which cannot be subjected to retort sterilization like PET bottles or paper packages, a process can be adopted, for example, such that the beverage is sterilized beforehand at a high temperature for a short time under similar sterilization conditions as those described above, for example, by a plate-type heat exchanger or the like, is cooled to a particular temperature, and is then filled in a package. Under aseptic conditions, additional ingredients may be added to and filled in a beverage-filled package. It is also possible to conduct an operation such that subsequent to heat sterilization under acidic conditions, the pH of the beverage is allowed to get back to neutral under aseptic conditions or that subsequent to heat sterilization under neutral conditions, the pH of the beverage is allowed to drop back to the acidic side under aseptic conditions.

No particular limitation is imposed on the form of each food according to the present invention insofar as it is in a palatable form. Illustrative are solid forms such as paste, powder, liquid, gel, slurry, agglomerates, granules, tablets, and capsules or the like. Depending upon the form of the food, the polyphenol composition according to the present invention may be subjected to reduced-pressure concentration, thin-film concentration or the like to remove its solvent, or may be converted into a powder form by spray drying or freeze drying or the like.

Examples of the food according to the present invention include confectioneries (e.g., breads, cakes, baked confections such as cookies and biscuits, chewing gums, chocolates, candies), desserts (e.g., jellys, yoghurts, ice creams), retort foods, and seasonings (e.g., sauces, soups, dressings, mayonnaises, creams).

The food according to the present invention may contain food additives commonly employed upon preparation of the food, for example, minerals, vitamins, amino acids, sweeteners, sour seasonings, flavorings, dried fruit or vegetable products, fruit juices, vegetable juices or their dried powder products, or the like can be added. Further, forming aids such as excipients, lubricants and coating agents may also be added.

EXAMPLES

1. Measurements of the Non-Polymer Catechins and Caffeine

A sample solution was filtered through a filter (0.45 µm). Using a high-performance liquid chromatograph (model: "SCL-10AVP"; manufactured by Shimadzu Corporation), a liquid chromatograph column packed with octadecyl group-introduced silica gel, "L-Column, TM ODS" (4.6 mm in diameter×250 mm; product of Chemicals Evaluation and Research Institute, Japan) was fitted. The filtered sample solution was then analyzed at a column temperature of 35° C. by the gradient elution method. A mobile phase, Solution A, was a solution containing acetic acid at 0.1 mol/L in distilled water, while another mobile phase, Solution B, was a solution containing acetic acid at 0.1 mol/L in acetonitrile. The measurement was conducted under the conditions of 20 µL sample injection volume and 280 nm UV detector wavelength. Gradient conditions were set as follows.

| Time (min) | Concentration of Solution A (vol %) | Concentration of Solution B (vol %) |
| --- | --- | --- |
| 0.0 | 97 | 3 |
| 5.0 | 97 | 3 |
| 37.0 | 80 | 20 |
| 43.0 | 80 | 20 |
| 43.5 | 0 | 100 |
| 48.5 | 0 | 100 |
| 49.0 | 97 | 3 |
| 60.0 | 97 | 3 |

2. Measurement of Rutin

A sample solution was filtered through a filter (0.45 µm). Using a high-performance liquid chromatograph (model: "Waters2695"; manufactured by Waters Corporation), a column ("Shimpack VP ODS", 150×4.6 mm I.D.) was fitted. The filtered sample solution was then analyzed at a column temperature of 40° C. by the gradient elution method. A mobile phase, Solution A, was a solution containing phosphoric acid at 0.05 wt % in distilled water, while another mobile phase, Solution B, was a methanol solution. The measurement was conducted under the conditions of 1 mL/min flow rate, 10 µL sample injection volume and 368 nm UV detector wavelength. Gradient conditions were set as follows.

| Time (min) | Concentration of Solution A (vol %) | Concentration of Solution B (vol %) |
| --- | --- | --- |
| 0.0 | 95 | 5 |
| 20.0 | 80 | 20 |
| 40.0 | 30 | 70 |
| 41.0 | 0 | 100 |
| 46.0 | 0 | 100 |
| 47.0 | 95 | 5 |
| 60.0 | 95 | 5 |

3. Measurements of Flavonol Aglycones (Myricetin, Quercetin and Kaempferol)

(1) Hydrolysis of Sample

To a sample solution (5 mL) which had been adjusted to a solids concentration of 0.2 wt %, mercaptoethanol (200 µL)

and 2 N hydrochloric acid (500 µL) were added. Subsequently, the mixture was heated at a preset temperature of 120° C. for 40 minutes in a dry block bath (manufactured by AS ONE CORPORATION) to hydrolyze flavonol glycosides in the sample into flavonol aglycones (myricetin, quercetin and kaempferol), followed by cooling.

(2) Analysis

The myricetin, quercetin and kaempferol, which existed in the sample solution after the hydrolysis, were quantitated by high-performance liquid chromatography. It is to be noted that the quantitation was conducted by the gradient elution method and that the analysis method was the same as in the above-described "measurement of rutin".

(3) Total Content of the Flavonol Aglycones

It was determined as the sum of the amounts of myricetin, quercetin and kaempferol as quantitated by the above-described analysis.

4. Measurement of Polyphenols (1) Preparation of Reagents

1) Preparation of ferrous tartrate reagent

Ferrous sulfate heptahydrate (0.50 g) and (+) sodium potassium tartrate tetrahydrate (2.50 g) were collected in a 500-mL graduated flask, and the total volume was increased with deionized water.

2) Preparation of phosphate buffer

Disodium hydrogenphosphate dihydrate (20.00 g) and potassium dihydrogenphosphate (2.90 g) were collected in a 2,000-mL graduated flask, and the total volume was increased with deionized water. The solution was adjusted such that its pH fell within a range of from 7.5 to 7.6. When the pH was higher than 7.6, a 0.9 g/100 mL aqueous solution of potassium dihydrogenphosphate dihydrate was added to adjust the pH. When the pH was lower than 7.5, on the other hand, a 1.2 g/100 mL aqueous solution of potassium dihydrogenphosphate was added to adjust the pH.

(2) Equipment and Instruments

1) Spectrophotometer ("U-2010", manufactured by Hitachi, Ltd.)

2) Quartz-made cells (10 mm×10 mm)

3) 25-mL, 100-mL, 200-mL, 500-mL and 2,000-mL graduated flasks 4) 1-mL, 5-mL, 10-mL, 20-mL and 30-mL transfer pipettes 5) 1-mL, 3-mL and 5-mL micropipettes (3) Analysis Conditions 1) Measurement wavelength: 540 nm 2) Temperature: 20° C.±2° C.

(4) Operation

1) Preparation of calibration line i) Ethyl gallate (approx. 0.5 g) was dried for 2 to 3 hours before use.

ii) The dried ethyl gallate (0.2 g) was weighed in a 200-mL graduated flask, and the total volume was increased with deionized water to provide a 100 mg/100 mL standard solution.

iii) Using the standard solution prepared in ii), 5 mg/100 mL, 10 mg/100 mL, 20 mg/100 mL and 30 mg/100 mL standard solutions were prepared in 100-mL graduated flasks, respectively.

iv) In 25-mL graduated flasks, 5 mL of the standard solutions prepared in iii) were weighted, respectively, followed by the addition of the ferrous tartrate reagent (5 mL). The total volumes were increased with the phosphate buffer. In addition, a solution without the addition of the standard solution was also prepared as a blank.

v) They were measured for absorbance by the spectrophotometer, and a calibration line was prepared.

The calibration line was prepared with reference to the following rough standards, and was readjusted when deviations occurred from them.

$R^2$: 0.9995 to 1.0000

Slope of calibration line: 34.5±0.4

Intercept: 0.3 or smaller

2) Measurement of Samples i) The zero-point of the spectrophotometer was corrected with deionized water.

ii) A predetermined amount of each sample was placed in a 25-mL graduated flask, followed by the addition of the ferrous tartrate reagent (5 mL). After the total volume was increased with the phosphate buffer, the absorbance was measured. The measurement of the absorbance was conducted within 40 minutes after the color reaction.

Example 1

Polyphenol Composition A

After green tea leaves (large leaf variety) were extracted with hot water, the extract solution was spray-dried to obtain a green tea extract A. In the green tea extract A, the concentration of the non-polymer catechins was 30.8 wt %, and the concentration of caffeine was 5.5 wt %.

The green tea extract A was then diluted with deionized water to lower the concentration of the non-polymer catechins to 1 wt %. For adsorption, the diluted solution (800 g) of the green tea extract A was allowed to pass through a column (50 mm I.D.×180 mm height, volume: 353.3 mL) packed with a synthetic adsorbent ("SP-70", product of Mitsubishi Chemical Corporation) (200 mL). Deionized water (300 mL) and a 30 wt % aqueous solution of ethanol (400 mL) were then allowed to successively pass through the synthetic adsorbent to elute the non-polymer catechins. Subsequently, a 50 wt % aqueous solution of ethanol (400 mL) was allowed to pass through the synthetic adsorbent to elute a polyphenol composition. It is to be noted that those fractionating operations were all conducted by adjusting the flow rate to give flow velocity (SV)=0.8 to 1.2 $[h^{-1}]$ and flow ratio (BV)=2.0 [v/v]. After insoluble matter was eliminated from the resulting eluate while distilling off the ethanol by reduced-pressure concentration, water was removed by freeze-drying to obtain a polyphenol composition A.

In the polyphenol composition A, the total content of the flavonol aglycones (A) was 19.2 wt %, the total content of the polyphenols (B) was 33.1 wt %, the weight ratio [(B)/(A)] was 1.72, and the content of rutin (C) was 10.6 wt %. The polyphenol composition A was used in inventive products 1 to 5 to be described subsequently herein.

Example 2

Polyphenol Composition B

After green tea leaves (large leaf variety) were extracted with hot water, the extract solution was spray-dried to obtain a green tea extract B. In the green tea extract B, the concentration of the non-polymer catechins was 30.3 wt %, and the concentration of caffeine was 5.5 wt %.

The green tea extract B was then diluted with deionized water to lower the concentration of the non-polymer catechins to 1 wt %. For adsorption, the diluted solution (8,000 g) of the green tea extract B was allowed to pass through a column (89.2 mm I.D.×600 mm height, volume: 3,748 mL)

packed with a synthetic adsorbent ("SP-70", product of Mitsubishi Chemical Corporation) (2,000 mL). Deionized water (3,000 mL) and a 25 wt % aqueous solution of ethanol (9,000 mL) were then allowed to successively pass through the synthetic adsorbent to elute the non-polymer catechins. Subsequently, a 92.5 wt %, aqueous solution of ethanol (4,000 mL) was allowed to pass through the synthetic adsorbent to elute a polyphenol composition. It is to be noted that those fractionating operations were all conducted by adjusting the flow rate to give flow velocity (SV)=0.5 to 2.1 [$^{-1}$] and flow ratio (BV)=2.0 [v/v]. After the ethanol was distilled off from the resulting eluate by reduced-pressure concentration, water was removed by freeze-drying to obtain a polyphenol composition B.

In the polyphenol composition B, the total content of the flavonol aglycones (A) was 18.3 wt %, the total content of the polyphenols (B) was 34.0 wt %, the weight ratio [(B)/(A)] was 1.86, and the content of rutin (C) was 9.3 wt %. The polyphenol composition B was used in an inventive product 6 to be described subsequently herein.

Example 3

Polyphenol Composition C

The green tea extract B obtained in Example 2 was diluted with deionized water to lower the concentration of the non-polymer catechins to 1 wt %. For adsorption, the diluted solution (2,400 g) of the green tea extract B was allowed to pass through a column (60.6 mm I.D.×330 mm height, volume: 951 mL) packed with a synthetic adsorbent ("SP-70", product of Mitsubishi Chemical Corporation) (600 mL). Deionized water (900 mL) and a 25 wt % aqueous solution of ethanol (2,700 mL) were then allowed to successively pass through the synthetic adsorbent to elute the non-polymer catechins. Subsequently, a 92.5 wt % aqueous solution of ethanol (1,200 mL) was allowed to pass through the synthetic adsorbent to elute a polyphenol composition. It is to be noted that those fractionating operations were all conducted by adjusting the flow rate to give flow velocity (SV)=0.7 to 1.8 [$^{-1}$] and flow ratio (BV)=2.0 [v/v]. After the ethanol was distilled off from the resulting eluate by reduced-pressure concentration, water was removed by freeze-drying to obtain a polyphenol composition C.

In the polyphenol composition C, the total content of the flavonol aglycones (A) was 23.3 wt %, the total content of the polyphenols (B) was 34.1 wt %, the weight ratio [(B)/(A)] was 1.46, and the content of rutin (C) was 7.4 wt %. The polyphenol composition C was used in an inventive product 7 to be described subsequently herein.

Example 4

Polyphenol Composition D

The polyphenol composition A (0.08 weight parts) obtained in Example 1 and a commercially-available green tea extract ("EGCg Preparation", product of DSM Nutritional Products Ltd., hereinafter called "the green tea extract a") (0.12 weight parts) were combined to obtain a polyphenol composition D. In the green tea extract a, the total content of the flavonol aglycones (A) was 0.0 wt %, and the total content of the polyphenols (B) was 110.5 wt %* (* analysis value by the ferrous tartrate method).

In the polyphenol composition D, the total content of the flavonol aglycones (A) was 7.7 wt %, the total content of the polyphenols (B) was 79.5 wt %, the weight ratio [(B)/(A)] was 10.32, and the content of rutin (C) was 4.2 wt %. The polyphenol composition D was used in an inventive product 8 to be described subsequently herein.

Example 5

Polyphenol Composition E

Commercially-available black tea leaves ("NUWARA ELIYA", product of Brooke Bond House) (5 g) were added to boiling water (500 g), and were extracted under stirring at 150 rpm for 5 minutes. The resulting mixture was filtered under suction through No. 2 filter paper, and the weight of the collected filtrate was measured, followed by ice-cooling (at liquid temperatures of 25° C. and lower). Subsequently, water was removed by freeze drying to obtain a black tea extract. The resultant black tea extract will hereinafter be called "the black tea extract a".

The black tea extract a (0.42 weight parts) and the polyphenol composition A (0.025 weight parts) obtained in Example 1 were combined to obtain a polyphenol composition E.

In the polyphenol composition E, the total content of the flavonol aglycones (A) was 1.9 wt %, the total content of the polyphenols (B) was 17.7 wt %, the weight ratio [(B)/(A)] was 9.32, and the content of rutin (C) was 1.3 wt %. The polyphenol composition E was used in an inventive product 9 to be described subsequently herein.

Example 6

Polyphenol Composition F

Commercially-available black tea leaves ("AS CTC", product of Brooke Bond House) (5 g) were added to boiling water (500 g), and were extracted under stirring at 150 rpm for 5 minutes. The resulting mixture was filtered under suction through No. 2 filter paper, and the weight of the collected filtrate was measured, followed by ice-cooling (at liquid temperatures of 25° C. and lower). Subsequently, water was removed by freeze drying to obtain a black tea extract. The resultant black tea extract will hereinafter be called "the black tea extract b".

The black tea extract b (0.39 weight parts) and the polyphenol composition A (0.025 weight parts) obtained in Example 1 were combined to obtain a polyphenol composition F.

In the polyphenol composition F, the total content of the flavonol aglycones (A) was 1.4 wt %, the total content of the polyphenols (B) was 13.3 wt %, the weight ratio [(B)/(A)] was 9.5, and the content of rutin (C) was 0.9 wt %. The polyphenol composition F was used in an inventive product 10 to be described subsequently herein.

Example 7

Polyphenol Composition G

Commercially-available oolong tea leaves ("OOLONG TEA", product of Kunitaro Co., Ltd.) (5 g) were added to boiling water (500 g), and were extracted under stirring at 150 rpm for 5 minutes. The resulting mixture was filtered under suction through No. 2 filter paper, and the weight of the collected filtrate was measured, followed by ice-cooling (at liquid temperatures of 25° C. and lower). Subsequently, water was removed by freeze drying to obtain an oolong tea extract. The resultant oolong tea extract will hereinafter be called "the oolong tea extract a".

The oolong tea extract a (0.39 weight parts) and the polyphenol composition A (0.025 weight parts) obtained in Example 1 were combined to obtain a polyphenol composition G.

In the polyphenol composition G, the total content of the flavonol aglycones (A) was 1.6 wt %, the total content of the polyphenols (B) was 14.7 wt %, the weight ratio [(B)/(A)] was 9.19 and the content of rutin (C) was 0.8 wt %. The polyphenol composition G was used in an inventive product 11 to be described subsequently herein.

Example 8

Polyphenol Composition H

The polyphenol composition A (0.05 weight parts) obtained in Example 1 and the green tea extract a (0.138 weight parts) were combined to obtain a polyphenol composition H.

In the polyphenol composition H, the total content of the flavonol aglycones (A) was 5.1 wt %, the total content of the polyphenols (B) was 89.9 wt %, the weight ratio [(B)/(A)] was 17.63 and the content of rutin (C) was 2.8 wt %. The polyphenol composition H was used in an inventive product 12 to be described subsequently herein.

Example 9

Polyphenol Composition I

The polyphenol composition A (0.01 weight parts) obtained in Example 1 and the black tea extract a (0.43 weight parts) were combined to obtain a polyphenol composition I.

In the polyphenol composition I, the total content of the flavonol aglycones (A) was 1.3 wt %, the total content of the polyphenols (B) was 17.2 wt %, the weight ratio [(B)/(A)] was 13.23 and the content of rutin (C) was 0.9 wt %. The polyphenol composition I was used in an inventive product 13 to be described subsequently herein.

Example 10

Polyphenol Composition J

The polyphenol composition A (0.01 weight parts) obtained in Example 1 and the black tea extract b (0.44 weight parts) were combined to obtain a polyphenol composition J.

In the polyphenol composition J, the total content of the flavonol aglycones (A) was 0.7 wt %, the total content of the polyphenols (B) was 12.5 wt %, the weight ratio [(B)/(A)] was 17.85 and the content of rutin (C) was 0.5 wt %. The polyphenol composition J was used in an inventive product 14 to be described subsequently herein.

Example 11

Polyphenol Composition K

The polyphenol composition A (0.01 weight parts) obtained in Example 1 and the oolong tea extract a (0.41 weight parts) were combined to obtain a polyphenol composition K.

In the polyphenol composition K, the total content of the flavonol aglycones (A) was 0.9 wt %, the total content of the polyphenols (B) was 14.0 wt %, the weight ratio [(B)/(A)] was 15.56 and the content of rutin (C) was 0.4 wt %. The polyphenol composition K was used in an inventive product 15 to be described subsequently herein.

Comparative Example 1

A commercially-available green tea extract ("POLYPHENONE 70A", product of Mitsui Norin Co., Ltd., hereinafter called "the green tea extract b") was used.

In the green tea extract b, the total content of the flavonol aglycones (A) was 1.1 wt %, the total content of the polyphenols (B) was 99.0 wt %, the weight ratio [(B)/(A)] was 90.00 and the content of rutin (C) was 0.1 wt %. The green tea extract b was used in a comparative product 1 to be described subsequently herein.

Comparative Example 2

The black tea extract a was used.

In the black tea extract a, the total content of the flavonol aglycones (A) was 0.9 wt %, the total content of the polyphenols (B) was 16.8 wt %, the weight ratio [(B)/(A)] was 18.67 and the content of rutin (C) was 0.7 wt %. The black tea extract a was used in a comparative product 2 to be described subsequently herein.

Comparative Example 3

The black tea extract b was used.

In the black tea extract b, the total content of the flavonol aglycones (A) was 0.3 wt %, the total content of the polyphenols (B) was 12.0 wt %, the weight ratio [(B)/(A)] was 40.00 and the content of rutin (C) was 0.2 wt %. The black tea extract b was used in a comparative product 3 to be described subsequently herein.

Comparative Example 4

The oolong tea extract a was used.

In the oolong tea extract a, the total content of the flavonol aglycones (A) was 0.5 wt %, the total content of the polyphenols (B) was 13.5 wt %, the weight ratio [(B)/(A)] was 27.00 and the content of rutin (C) was 0.1 wt %. The oolong tea extract a was used in a comparative product 4 to be described subsequently herein.

Comparative Example 5

With a 0.15 wt % aqueous solution of sodium bicarbonate (95° C.), oolong tea leaves (600 g) were extracted by the column method to obtain an extract (approx. 6,000 g). While the temperature of the extract solution was maintained at from 60 to 65° C., it was passed through a granular activated carbon ("GW-H32/60", product of Kuraray Co., Ltd.) (400 g) to selectively remove the non-polymer catechins and caffeine. The resulting solution by the pass was concentrated under reduced pressure to prepare a tea extract having a Brix degree of 10 or greater (approx. 900 g), whereby an oolong tea extract b was obtained.

In the oolong tea extract b, the total content of the flavonol aglycones (A) was 0.84 wt %, the total content of the polyphenols (B) was 19.4 wt %, the weight ratio [(B)/(A)] was 23.1 and the content of rutin (C) was 0.18 wt %. The oolong tea extract b was used in a comparative product 5 to be described subsequently herein.

Comparative Example 6

Production of Green Tea Extract c

A concentrated green tea extract ("POLYPHENONE HG", product of Mitsui Norin Co., Ltd.) (200 g) was dispersed in a 40 wt % aqueous solution of ethanol (800 g) under stirring conditions of 250 r/min at 25° C. After acid clay ("MIZUKA ACE #600", product of Mizusawa Chemical Industries, Ltd.) (80 g) was charged, stirring was continued for approx. 10 minutes. Subsequent to filtration through No. 2 filter paper, activated carbon (8 g) was added to the filtrate, and the mixture was filtered again through No. 2 filter paper. The filtrate was then refiltered through a 0.2-µm membrane filter. The ethanol was distilled off at 40° C. under reduced pressure, and the concentration of the non-polymer catechins was adjusted with deionized water to obtain a green tea extract c.

In the green tea extract c, the total content of the flavonol aglycones (A) was 1.5 wt %, the total content of the polyphenols (B) was 47.7 wt %, the weight ratio [(B)/(A)] was 32.49 and the content of rutin (C) was 0.96 wt %. The green tea extract c was used in a comparative product 6 to be described subsequently herein.

Evaluation of Taste and Flavor

The individual ingredients shown in Tables 1 and 2 were separately weighed in the added amounts in sample bottles, into which deionized water was charged to disperse the ingredients. In a water bath controlled at 60° C., the ingredients were then dissolved. The resulting solutions were allowed to stand at room temperature (25° C.) for 2 hours to prepare beverages. When the individual beverages had been allowed to be controlled to room temperature, a sensory test was conducted according to the below-described standards. The results are shown in Tables 1 and 2.

(Evaluation Standards)
5: Very good (Highly-palatable bitterness is felt, and harshness is minimal).
4: Good (Harshness is felt, but does not bother).
3. Slightly good (Harshness slightly bothers).
2. Slightly bad (Harshness is a little strong).
1. Bad (Harshness is strong).

TABLE 1

|  |  | Inventive products | | | | | | | |
|---|---|---|---|---|---|---|---|---|---|
|  |  | 1 | 2 | 3 | 4 | 5 | 6 | 7 | 8 |
| Formulations of beverages | Polyphenol composition A (wt %) | 0.05 | 0.20 | 0.50 | 1.00 | 2.00 | — | — | 0.08 |
|  | Polyphenol composition B (wt %) | — | — | — | — | — | 0.20 | — | — |
|  | Polyphenol composition C (wt %) | — | — | — | — | — | — | 0.20 | — |
|  | Green tea extract a (wt %) | — | — | — | — | — | — | — | 0.12 |
|  | Green tea extract b (wt %) | — | — | — | — | — | — | — | — |
|  | Green tea extract c (wt %) | — | — | — | — | — | — | — | — |
|  | Black tea extract a (wt %) | — | — | — | — | — | — | — | — |
|  | Black tea extract b (wt %) | — | — | — | — | — | — | — | — |
|  | Oolong tea extract a (wt %) | — | — | — | — | — | — | — | — |
|  | Oolong tea extract b (wt %) | — | — | — | — | — | — | — | — |
|  | Deionized water | Balance | | | | | | | |
|  | Total (wt %) | 100 | 100 | 100 | 100 | 100 | 100 | 100 | 100 |
| Composition analysis data of solids in beverages | (A) Total content of the flavonol aglycones (wt %) | 19.2 | 19.2 | 19.2 | 19.2 | 19.2 | 18.3 | 23.3 | 7.7 |
|  | (B) Total content of the polyphenols (wt %) | 33.1 | 33.1 | 33.1 | 33.1 | 33.1 | 34.0 | 34.1 | 79.5 |
|  | (C) Total content of rutin (wt %) | 10.6 | 10.6 | 10.6 | 10.6 | 10.6 | 9.3 | 7.4 | 4.2 |
|  | Weight ratio [(B)/(A)] | 1.72 | 1.72 | 1.72 | 1.72 | 1.72 | 1.86 | 1.46 | 10.32 |
| Evaluation of taste and flavor |  | 5 | 5 | 5 | 4 | 4 | 5 | 5 | 4 |

|  |  | Inventive products | | | | | |
|---|---|---|---|---|---|---|---|
|  |  | 9 | 10 | 11 | 12 | 13 | 14 | 15 |
| Formulations of beverages | Polyphenol composition A (wt %) | 0.025 | 0.025 | 0.025 | 0.05 | 0.01 | 0.01 | 0.01 |
|  | Polyphenol composition B (wt %) | — | — | — | — | — | — | — |
|  | Polyphenol composition C (wt %) | — | — | — | — | — | — | — |
|  | Green tea extract a (wt %) | — | — | — | 0.138 | — | — | — |

TABLE 1-continued

|  |  |  |  |  |  |  |  |  |
|---|---|---|---|---|---|---|---|---|
|  | Green tea extract b (wt %) | — | — | — | — | — | — | — |
|  | Green tea extract c (wt %) | — | — | — | — | — | — | — |
|  | Black tea extract a (wt %) | 0.42 | — | — | — | 0.43 | — | — |
|  | Black tea extract b (wt %) | — | 0.39 | — | — | — | 0.44 | — |
|  | Oolong tea extract a (wt %) | — | — | 0.39 | — | — | — | 0.41 |
|  | Oolong tea extract b (wt %) | — | — | — | — | — | — | — |
|  | Deionized water | Balance | | | | | | |
|  | Total (wt %) | 100 | 100 | 100 | 100 | 100 | 100 | 100 |
| Composition analysis data of solids in beverages | (A) Total content of the flavonol aglycones (wt %) | 1.9 | 1.4 | 1.6 | 5.1 | 1.3 | 0.7 | 0.9 |
|  | (B) Total content of the polyphenols (wt %) | 17.7 | 13.3 | 14.7 | 89.9 | 17.2 | 12.5 | 14.0 |
|  | (C) Total content of rutin (wt %) | 1.3 | 0.9 | 0.8 | 2.8 | 0.9 | 0.5 | 0.4 |
|  | Weight ratio [(B)/(A)] | 9.32 | 9.5 | 9.19 | 17.63 | 13.23 | 17.85 | 15.56 |
| Evaluation of taste and flavor |  | 4 | 4 | 4 | 3 | 3 | 3 | 3 |

TABLE 2

|  |  | Comparative products | | | | | |
|---|---|---|---|---|---|---|---|
|  |  | 1 | 2 | 3 | 4 | 5 | 6 |
| Formulations of beverages | Polyphenol composition A (wt %) | — | — | — | — | — | — |
|  | Polyphenol composition B (wt %) | — | — | — | — | — | — |
|  | Polyphenol composition C (wt %) | — | — | — | — | — | — |
|  | Green tea extract a (wt %) | — | — | — | — | — | — |
|  | Green tea extract b (wt %) | 1.00 | — | — | — | — | — |
|  | Green tea extract c (wt %) | — | — | — | — | — | 1.00 |
|  | Black tea extract a (wt %) | — | 0.44 | — | — | — | — |
|  | Black tea extract b (wt %) | — | — | 0.48 | — | — | — |
|  | Oolong tea extract a (wt %) | — | — | — | 0.42 | — | — |
|  | Oolong tea extract b (wt %) | — | — | — | — | 0.48 | — |
|  | Deionized water | Balance | | | | | |
|  | Total (wt %) | 100 | 100 | 100 | 100 | 100 | 100 |
| Composition analysis data of solids in beverages | (A) Total content of the flavonol aglycones (wt %) | 1.1 | 0.9 | 0.3 | 0.5 | 0.84 | 1.5 |
|  | (B) Total content of the polyphenols (wt %) | 99.0 | 16.8 | 12.0 | 13.5 | 19.4 | 47.7 |
|  | (C) Total content of rutin (wt %) | 0.1 | 0.7 | 0.2 | 0.1 | 0.18 | 0.96 |
|  | Weight ratio [(B)/(A)] | 90.00 | 18.67 | 40.00 | 27.00 | 23.10 | 32.49 |
| Evaluation of taste and flavor |  | 1 | 2 | 1 | 1 | 2 | 2 |

From Tables 1 and 2, it has been found that compared with the conventional extracts of *Camellia sinensis*, the polyphenol compositions, in each of which the weight ratio [(B)/(A)] of the total content of the polyphenols (B) to the total content of the flavonols (A) was from 0.01 to 18, were markedly reduced in the harshness inherent to the polyphenols, were good in taste and flavor, and were also good in palatability.

Evaluation of Baked Confections

Baked confections were made using the polyphenol composition A of Example 1.

Materials α [skim milk powder (25 weight parts), unsalted butter (25 weight parts), white sugar (29 weight parts), and margarine (45 weight parts)] were weighed, placed in a mixer ["N50 MIXER" (5-quart mixer), manufactured by Hobart Food Equipment Pty Ltd.], stirred at low speed for 30 seconds by a beater, and then stirred at medium speed to prepare a dough having a specific gravity of 0.9.

One third of beaten eggs were then added while the materials α were stirred at low speed for 30 seconds. After the addition of the first one-third of the beaten eggs, stirring was conducted at low speed for 30 seconds. Upon addition of the second one-third of the beaten eggs, water and beaten eggs in which salt was dissolved and the polyphenol composition A were directly charged into the mixer at the same time, followed by stirring at low speed for 30 seconds. After completion of the stirring, oil matter adhered on a wall of the mixer was scraped down. Subsequently, the remaining one-third of the beaten eggs was added, stirred at low speed for 30 seconds, and then stirred at medium speed for 2 minutes until homogeneous and creamy.

Soft wheat flour was next added, followed by stirring at low speed for 45 seconds. A dough obtained by the stirring was weighed into 20 g portions, which were filled in rectangular baking molds of 72 mm long×22 mm wide×14 mm height, respectively. The filled, rectangular baking molds were arranged on baking trays with bakery release paper laid thereon. Through the surface of the dough filled in each baking mold, six holes were pierced with toothpicks. On each baking tray, the filled, rectangular baking molds were arranged in 3 rows with 4 molds per row, that is, as many as 12 molds in total. Under the baking tray, two baking trays were then additionally placed one over the other, and an aluminum foil was applied over the surface of each baking mold. Baking was carried out in an oven at 160° C. The baking was carried out for 20 minutes with the aluminum foil being still applied, and subsequent to removal of the aluminum foil, the baking was continued further for 18 minutes to make baked confections. After the baking, the baked confections were allowed to cool at room temperature for 20 minutes on a wire rack, packed in a zipper polyethylene bag, and then stored overnight in a constant-temperature chamber controlled at 20° C. As a result of a texture evaluation, the baked confections were found to be edible without noticing any problem on their texture.

Test Example 1

Effect for the Suppression of Increase in Postprandial Blood Glucose Level

Male mice C57BL/6J (7 weeks old) were provisionally reared for 6 days, and after fasted for 16 hours before the beginning of the test, were divided into 4 groups (Ex-1 group, Comp Ex-6 group, Comp Ex-5 group, Control group (water); n=5 in each group), followed by the collection of blood.

To the Ex-1 group, the preparation obtained in Example 1 was dissolved in a 20 wt % aqueous solution of ethanol, and the resulting solution was orally administered at 0.57 mg/g-body weight. To the Comp Ex-6 group, the preparation obtained in Comparative Example 6 was dissolved in a 20 wt % aqueous solution of ethanol, and the resulting solution was orally administered at 0.39 mg/g-body weight. Further, to the Comp Ex-5 group, the preparation obtained in Comparative Example 5 was dissolved in a 20 wt % aqueous solution of ethanol, and the resulting solution was orally administered at 1.00 mg/g-body weight. To the control group, on the other hand, 20 wt % ethanol was orally administered. To the mice shortly after the administration of the respective samples, a fat emulsion of the composition shown in Table 3 was orally administered to give an administration rate of 40 mg/g-body weight.

TABLE 3

| Olive oil | 5 wt % |
| Starch | 5 wt % |
| Albumin | 0.1 wt % |
| Water | 89.9 wt % |

Upon elapsed time of 10 minutes, 30 minutes, 60 minutes and 120 minutes after the administration of the fat emulsion, blood were collected from the individual mice, and with "GLUCOSE CII-TEST WAKO" (product of Wako Pure Chemical Industries, Ltd.), were analyzed for blood glucose level. Changes in postprandial blood glucose level are illustrated in FIG. 1. Signs a, b, and c indicate the existence of significant differences among the graphs.

From FIG. 1, the following conclusions have been confirmed. Described specifically, it has been found that by the administration of the fat emulsion, the postprandial blood glucose level increased in the control group and took a similar value in the Comp Ex-5 group, and such an increase in postprandial blood glucose level was suppressed in both the Ex-1 group and the Comp Ex-6 group and also the increase in postprandial blood glucose level was remarkably suppressed in the Ex-1 group compared with the Comp Ex-6 group.

Test Example 2

Effect for the Inhibition of α-amylase Activity

Measurement of α-amylase activity was conducted by the following method.
Enzyme: 50 U/mL Swine pancreas amylase (dissolved in buffer)
Substrate: 20 mg Starch Azure (in 80 μL buffer)
Buffer: 40 mM Phosphate buffer (with 20 mM NaCl contained therein) (pH 7.0)
Inhibitors: The preparation (test sample) obtained in Example 1 or the preparations (control samples) obtained in Comparative Examples 5 and 6 (dissolved in 20% EtOH)
Procedure:
(1) The substrate (20 mg/80 μL) and inhibitor (10 μL) were combined in equal amounts, and then were preincubated at 37° C. for 15 minutes.
(2) The enzyme solution (10 μL) was added, and reacted at 37° C. for 15 minutes.
(3) A 100 mM phosphate buffer (pH 4.3) (900 μL) was added.
(4) The reaction mixture was centrifuged, and the supernatant was measured at 595 nm wavelength.

Figure 2:
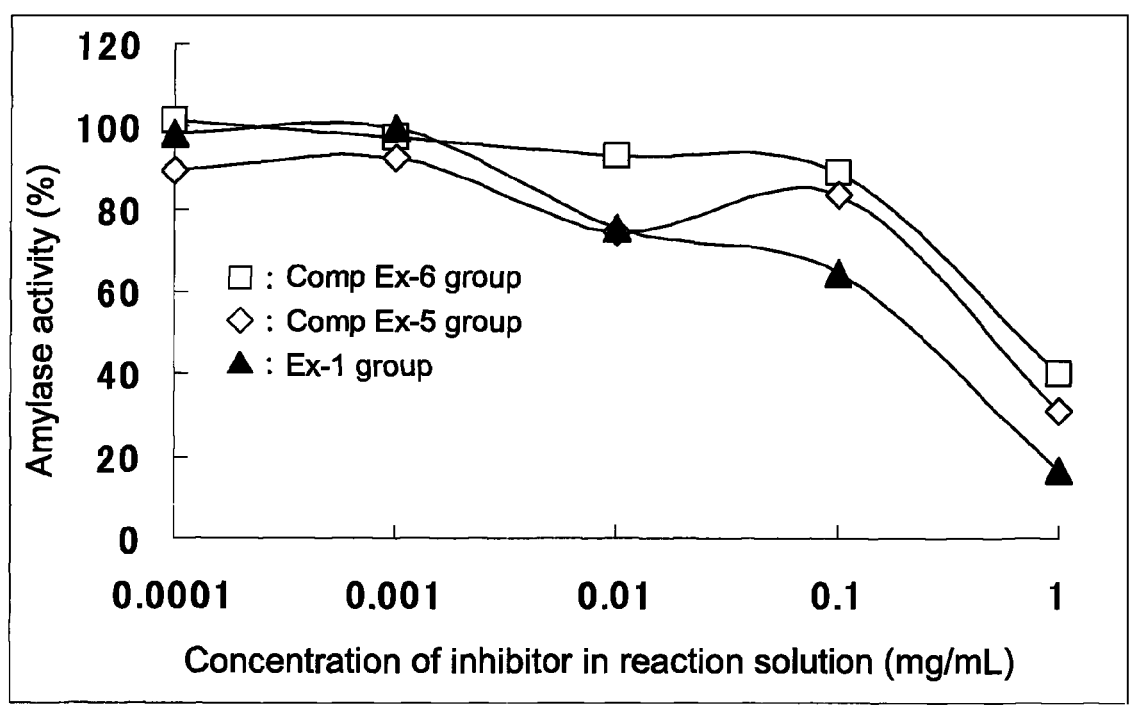
FIG. 2 is a diagram illustrating an effect for the inhibition of α-amylase activity in Test Example 2.

The results of the measurement are illustrated in FIG. 2. It has been found from FIG. 2 that the Ex-1 group strongly inhibited α-amylase activity compared with the Comp Ex-6 group and Comp Ex-5 group.

Test Example 3

Effect for the Inhibition of Lipase Activity

Measurement of lipase activity was conducted by the following method.
Enzyme: 50 U/mL Swine pancreas lipase ("SIGMA TYPE II" dissolved in buffer)

Substrate: 0.1 M 4-Methylumbelliferyl oleate (dissolved in DMSO)
Buffer: 13 mM Tris-HCl (pH 8.0) containing 150 mM NaCl and 1.36 mM $CaCl_2$
Inhibitors: The preparation obtained in Example 1 or the preparations obtained in Comparative Examples 5 and 6 (dissolved in 20% EtOH)
Procedure:
(1) At 25° C., the buffer (60 μL) and substrate (20 μL) were added to a microplate and were combined thereon.
(2) The inhibitors (10 μL) was added.
(3) The enzyme (10 μL) was added.
(4) Incubation was conducted at 25° C. for 30 minutes.
(5) A stop solution (citrate buffer, pH 4.2) (100 μL) was added.
(6) Fluorescence was measured at 460 nm wavelength (with 355 nm excitation wavelength).

Figure 3:
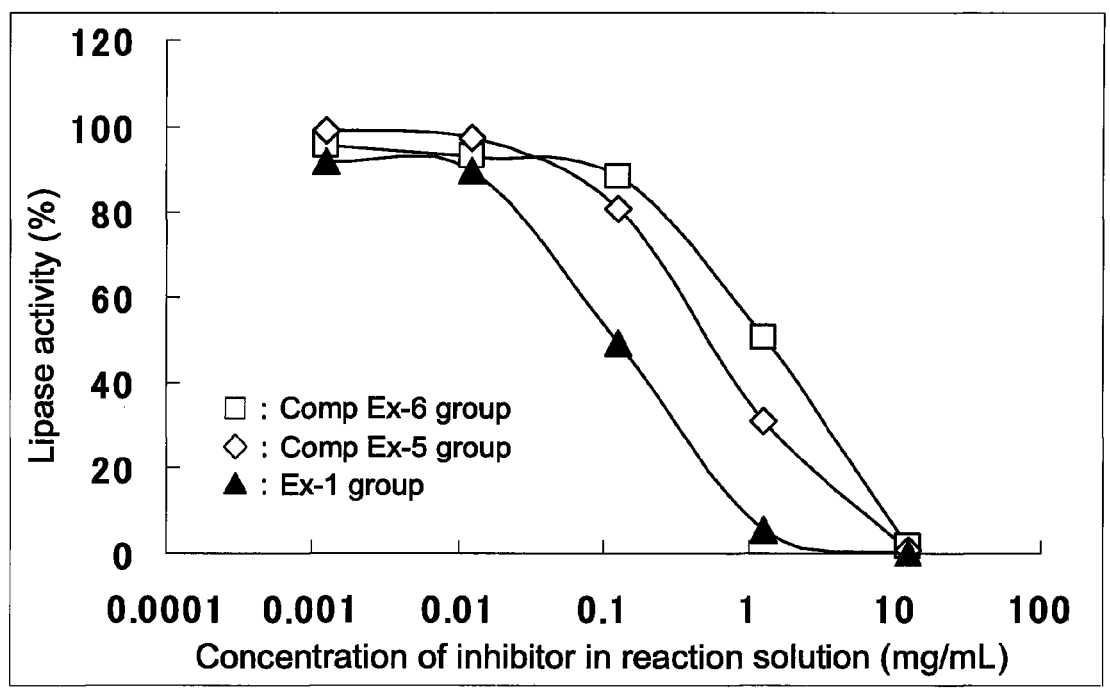
FIG. 3 is a diagram illustrating an effect for the inhibition of lipase activity in Test Example 3.

The results of the fluorescence measurement are illustrated in FIG. 3. It has been found from FIG. 3 that the Ex-1 group strongly inhibited lipase activity compared with the Comp Ex-6 group and Comp Ex-5 group.

From these Test Examples, it finds that the polyphenol composition according to the present invention has excellent effects for the suppression of an increase in postprandial blood glucose level, for the inhibition of α-amylase activity and for the inhibition of lipase activity. Therefore, the polyphenol composition according to the present invention is useful as an active ingredient in a medicament for the suppression of absorption of dietary fat, for the reduction of an increase in blood neutral fat, for the prevention of obesity, or the like.

The invention claimed is:

1. A process for the production of a polyphenol composition derived from *Camellia sinensis* and comprising a flavonol aglycone and a flavonol glycoside, wherein:
   a weight ratio [(B)/(A)] of the total contents (B) to (A) is from 1.46 to 11:
   (A) is a total content of the flavonol aglycone present in solids of the polyphenol composition after hydrolysis as measured by high-performance liquid chromatography, and
   (B) is a total content of the polyphenol present in solids of the polyphenol composition as measured by the ferrous tartrate method,
   the process comprising treating a *Camellia sinensis* extract so as to obtain said ratio.

2. The process according to claim 1, wherein the total content of the flavonol aglycone (A) is from 0.7 to 50 wt %.

3. The process according to claim 2, wherein the total content of the polyphenol (B) is from 5 to 95 wt %.

4. The process according to claim 2, wherein the polyphenol composition further comprises rutin, and (C) a content of rutin present in the solids of the polyphenol composition is from 0.4 to 30 wt %.

5. The process according to claim 2, wherein the *Camellia sinensis* is green tea.

6. The process according to claim 1, wherein the total content of the polyphenol (B) is from 5 to 95 wt %.

7. The process according to claim 1, wherein the polyphenol composition further comprises rutin, and (C) a content of rutin present in the solids of the polyphenol composition is from 0.4 to 30 wt %.

8. The process according to claim 1, wherein the *Camellia sinensis* is green tea.

9. The process according to claim 1, wherein the total content of the flavonol aglycone (A) is from 1.5 to 45 wt %.

10. The process according to claim 1, wherein the total content of the flavonol aglycone (A) is from 5 to 40 wt %.

11. The process according to claim 1, wherein the total content of the flavonol aglycone (A) is from 7 to 35 wt %.

12. The process according to claim 1, wherein the total content of the flavonol aglycone (A) is from 9 to 25 wt %.

13. The process according to claim 1, wherein the total content of the polyphenol (B) is from 10 to 90 wt %.

14. The process according to claim 1, wherein the total content of the polyphenol (B) is from 15 to 80 wt %.

15. The process according to claim 1, wherein the total content of the polyphenol (B) is from 20 to 70 wt %.

16. The process according to claim 1, wherein the total content of the polyphenol (B) is from 25 to 40 wt %.

17. The process according to claim 1, wherein the weight ratio [(B)/(A)] is from 1.46 to 9.

18. The process according to claim 1, wherein the weight ratio [(B)/(A)] is from 1.46 to 7.

19. The process according to claim 1, wherein the weight ratio [(B)/(A)] is from 1.46 to 5.

20. The process according to claim 1, wherein the weight ratio [(B)/(A)] is from 1.72 to 11.

* * * * *